(12) United States Patent
Kim et al.

(10) Patent No.: US 10,141,577 B2
(45) Date of Patent: Nov. 27, 2018

(54) MANUFACTURING METHOD FOR CATALYST ELECTRODE, CATALYST ELECTRODE MANUFACTURED BY MEANS OF METHOD, AND BATTERY COMPRISING SAME

(75) Inventors: Jungbae Kim, Seoul (KR); Jinwoo Lee, Gyeongsangbuk-do (KR); Chulmin Jeon, Daejeon (KR); Jongmin Shim, Busan (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 468 days.

(21) Appl. No.: 14/113,442

(22) PCT Filed: May 23, 2012

(86) PCT No.: PCT/KR2012/004054
§ 371 (c)(1),
(2), (4) Date: Nov. 26, 2013

(87) PCT Pub. No.: WO2012/161503
PCT Pub. Date: Nov. 29, 2012

(65) Prior Publication Data
US 2014/0080011 A1    Mar. 20, 2014

(30) Foreign Application Priority Data
May 23, 2011 (KR) .................. 10-2011-0048439

(51) Int. Cl.
*H01M 4/86* (2006.01)
*H01M 8/16* (2006.01)
(Continued)

(52) U.S. Cl.
CPC ...... *H01M 4/8626* (2013.01); *G01N 27/4075* (2013.01); *H01M 4/8807* (2013.01);
(Continued)

(58) Field of Classification Search
CPC .... H01M 4/86; H01M 4/8626; H01M 4/8807; H01M 4/8817; H01M 4/8803;
(Continued)

(56) References Cited

U.S. PATENT DOCUMENTS 3,899,354 A * 8/1975 Kordesch ................ H01M 4/86
29/623.1
6,812,187 B1  11/2004 Pak et al.
(Continued)

FOREIGN PATENT DOCUMENTS

KR    10-0474854 B1    3/2005

OTHER PUBLICATIONS

Guo, C., et al., "High-performance biofuel cell made with hydrophilic ordered mesoporous carbon as electrode material", "Journal of Power Sources", Feb. 4, 2010, pp. 4090-4097, vol. 195.*
(Continued)

*Primary Examiner* — Jimmy Vo
(74) *Attorney, Agent, or Firm* — Hultquist, PLLC; Steven J. Hultquist

(57) ABSTRACT

The catalytic electrode of the present invention does not cause electron transfer resistance, unlike conventional catalytic electrodes coated with Nafion or the like, and thus can achieve significantly high electron transfer efficiency. Accordingly, the catalytic electrode can have high power density, and thus has excellent physical properties.

16 Claims, 11 Drawing Sheets

(51) Int. Cl.
*H01M 4/88* (2006.01)
*H01M 8/0234* (2016.01)
*H01M 8/0239* (2016.01)
*H01M 8/0241* (2016.01)
*G01N 27/407* (2006.01)
*G01N 27/327* (2006.01)

(52) U.S. Cl.
CPC ....... H01M 4/8878 (2013.01); H01M 8/0234 (2013.01); H01M 8/0239 (2013.01); H01M 8/0241 (2013.01); H01M 8/16 (2013.01); G01N 27/3272 (2013.01); H01M 4/8817 (2013.01); Y02E 60/527 (2013.01)

(58) Field of Classification Search
CPC ............. H01M 4/8878; H01M 4/0234; H01M 4/0239; H01M 4/0241; H01M 8/0234; H01M 8/0239; H01M 8/0241; H01M 8/16; B01J 21/18

USPC .................... 429/529, 535, 401; 204/403.14
See application file for complete search history.

(56) References Cited

U.S. PATENT DOCUMENTS 7,718,570 B2   5/2010   Pak et al.
2009/0136808 A1*   5/2009   Kang ...................... B01J 21/18
                                                                  429/532

OTHER PUBLICATIONS

Lee, D., et al., "Simple Fabrication of a Highly Sensitive and Fast Glucose Biosensor Using Enzymes Immobilized in Mesocellular Carbon Foam", "Advanced Materials", 2005, pp. 2828-2833, vol. 17.*

* cited by examiner

MANUFACTURING METHOD FOR CATALYST ELECTRODE, CATALYST ELECTRODE MANUFACTURED BY MEANS OF METHOD, AND BATTERY COMPRISING SAME

CROSS-REFERENCE TO RELATED APPLICATIONS

This application is a U.S. national phase under the provisions of 35 U.S.C. § 371 of International Patent Application No. PCT/KR12/004054 filed May 23, 2012, which in turn claims priority of Korean Patent Application No. 10-2011-0048439 filed May 23, 2011. The disclosures of such international patent application and Korean priority patent application are hereby incorporated herein by reference in their respective entireties, for all purposes.

TECHNICAL FIELD

The present invention relates to a method of preparing a catalytic electrode, a catalytic electrode fabricated thereby and a cell comprising the same, and more particularly to a method of preparing a catalytic electrode, in which the fixing and stability of a catalyst on an electrode support can be increased to maximize electron transfer efficiency, a catalytic electrode fabricated thereby and a cell comprising the same.

BACKGROUND ART

When fabricating electrodes for most $H_2/O_2$ fuel cells or sensors, Nafion (DuPont, perfluorinated sulfonic acid polymer) is used as a binder for fixing a catalyst to the electrode surface. Particularly, enzyme electrodes comprising Nafion have been developed in various ways. FIG. 1 is a perspective view of a conventional biofuel cell wherein an anode and a cathode are separated from each other by a proton exchange membrane. A method has been proposed in which the surface of a carbon electrode is coated with Nafion for the dispersion and adsorption of a catalyst and the dispersion of nanostructured materials and an enzyme is attached to the coated Nafion. However, this method entails a problem in that the enzyme is exposed to the external environment so that the enzymatic activity rapidly decreases.

To overcome this problem, a method has been proposed in which an enzyme is entrapped between a carbon electrode and a Nafion membrane by adsorbing the enzyme onto carbon paper, followed by coating with Nafion. However, this method encounters problems in that the enzyme is not uniformly dispersed and it is difficult for the electrons generated in the enzyme electrode by the Nafion membrane to reach directly a current collector.

Accordingly, a method is currently used in which an enzyme is entrapped in a Nafion membrane by immersing carbon paper in a solution mixture of the enzyme and a Nafion solution. This method is advantageous in terms of the dispersion of the enzyme and the stability of the electrode, but involves a problem in that the Nafion reduces the lifespan and activity of the enzyme and interferes with the transfer of the electrons generated in the enzyme electrode to a current collector.

DISCLOSURE OF INVENTION

It is an object of the present invention to provide a catalytic electrode, which can achieve high electron transfer efficiency while eliminating electron transfer resistance caused by Nafion, and a fabrication method thereof.

To achieve the above object, the present invention provides a method of preparing a catalytic electrode, the method comprising the steps of:

(1) preparing a solution mixture including an electroconductive precursor, a pore support precursor, and a continuous pore forming agent;

(2) immersing an electrode support in the solution mixture to form a matrix filled in or coated on the electrode support;

(3) calcining the matrix to remove the continuous pore forming agent and form continuous pores in the matrix; and (4) loading a catalyst into the continuous pores in the matrix.

According to a preferred embodiment of the present invention, the electroconductive precursor may include one or more precursors selected from the group consisting of a carbon precursor, a palladium precursor, and a platinum precursor. The carbon precursor that is used in the present invention may preferably be one or more selected from the group consisting of resole, furfuryl alcohol, phenol-formaldehyde resin, resorcinol-formaldehyde resin, sucrose, pitch, and coal tar.

According to another preferred embodiment of the present invention, the pore support precursor may be either silicone alkoxide or organosilicate. According to still another preferred embodiment of the present invention, the continuous pore forming agent may be an amphiphilic block copolymer.

According to still another preferred embodiment of the present invention, the amphiphilic block copolymer may include, as a hydrophilic block, one or more selected from the group consisting of polystyrene-b-poly(ethylene oxide), PS-b-PEO, polyisoprene-b-poly(ethlyene oxide), poly(ethylene oxide)-poly(propylene oxide)-poly(ethlyene oxide), poly(ethylene oxide), and poly(oligo(ethylene glycol)methacrylate) (POEGMA), and as a hydrophobic block, one or more selected from the group consisting of poly(styrene), poly(isoprene), and poly(methyl methacrylate).

According to still another preferred embodiment of the present invention, the weight ratio of the continuous pore forming agent to the sum of the electroconductive precursor and the pore support precursor may be 1:3 to 1:6 or 1:1 to 4:1.

According to still another preferred embodiment of the present invention, the solution mixture may include, based on 100 parts by weight of a solvent, 0.5-30 parts by weight of the electroconductive precursor, 0.5-30 parts by weight of the pore support precursor, and 0.5-10 parts by weight of the continuous pore forming agent.

According to still another preferred embodiment of the present invention, the electrode support may be a carbon fibrous assembly or a silica structure.

According to still another preferred embodiment of the present invention, the carbon fibrous assembly may be carbon paper, carbon felt, or carbon cloth.

According to still another preferred embodiment of the present invention, some or all of the continuous pores may be connected with each other.

According to still another preferred embodiment of the present invention, the size of the continuous pores may be 1-1000 nm.

According to still another preferred embodiment of the present invention, the continuous pores may be formed by a self-assembled continuous pore forming agent.

According to still another preferred embodiment of the present invention, the method may further comprise, between steps (3) and (4), a step of removing the pore support precursor.

According to still another preferred embodiment of the present invention, the catalyst may be either an enzyme or a metal catalyst. Herein, the enzyme may be one or more selected from the group consisting of glucose oxidase, glucose dehydrogenase, pyranose dehydrogenase, alcohol dehydrogenase, aldehyde dehydrogenase, formate dehydrogenase, diaphorase, microperoxidase-11, lactated dehydrogenase, hydrogenase, catalase, tyrosinase, laccase, cytochrome oxidase, soybean peroxidase, cytochrome c oxidase, chloroperoxidase, horseradish peroxidase, and bilirubin oxidase, and the metal catalyst may be one or more selected from the group consisting of platinum, ruthenium, osmium, palladium, and alloys thereof.

According to still another preferred embodiment of the present invention, there is provided an electrode structure comprising: an electrode support; and an electroconductive material including continuous pores which are filled in or coated on the electrode support and is capable of being loaded with a catalyst.

According to still another preferred embodiment of the present invention, the electroconductive material may be a continuous phase.

According to still another preferred embodiment of the present invention, the electrode support may be a carbon assembly or a silica structure.

According to still another preferred embodiment of the present invention, the electroconductive material may include one or more materials selected from the group consisting of carbon, palladium, and platinum.

According to still another preferred embodiment of the present invention, the continuous pores may be ordered, and the diameter of the continuous pores may be 1-1000 nm.

According to still another preferred embodiment of the present invention, some or all of the continuous pores may be connected with each other.

According to still another preferred embodiment of the present invention, there is provided a catalytic electrode including a catalyst in the continuous pores of an electrode support structure, wherein the catalyst may be either an enzyme or a metal catalyst.

According to still another preferred embodiment of the present invention, the enzyme may be covalently bonded to the inside of the continuous pores of the electrode structure or may include a crosslinked enzyme aggregate having a diameter greater than the entrance size of the continuous pores.

According to still another preferred embodiment of the present invention, the average pore size of the continuous pores may be 0.5-5 nm greater than the diameter of the catalyst, and the loading amount of the catalyst may be 10-100% of the total volume of pores that are capable of being loaded with the catalyst.

According to still another preferred embodiment of the present invention, the average distance from the surface of the enzyme to the inner surface of the continuous pores may be 10 nm or less, and electrons produced in the enzyme may be transferred directly to the inner surface of the continuous pores or may not be released to the outside of the continuous pores.

According to still another preferred embodiment of the present invention, there is provided a cell selected from the group consisting of a fuel cell, a biofuel cell, a solar cell, a secondary cell, and a supercapacitor, which comprise the catalytic electrode of the present invention.

According to still another preferred embodiment of the present invention, there is provided a biosensor comprising the catalytic electrode of the present invention.

According to still another preferred embodiment of the present invention, the cell may include no perfluorinated sulfonic acid polymer (Nafion).

ADVANTAGEOUS EFFECT

The catalytic electrode of the present invention can achieve a significantly high electron transfer efficiency compared to conventional catalytic electrodes prepared using Nafion or the like. Specifically, electrons produced by the reaction of the catalyst loaded in the continuous pores are easily transferred directly or through the electrode support entrained in the electroconductive matrix to the current collector. Thus, in the present invention, an efficient electron transfer system which was impossible in most catalytic electrodes comprising Nafion was first realized. This catalytic electrode based on efficient electron transfer may have high power density, and thus has excellent physical properties.

Also, when no Nafion is used, resistance to the mass transfer of fuel or a sample, which is caused by a Nafion membrane, does not occur, and thus power density can be increased. Accordingly, the catalytic electrode of the present invention may have high power density, and thus has excellent physical properties.

The catalytic electrode of the present invention allows high catalyst loading to be achieved by suitably controlling continuous pores for each of various catalysts. Thus, the catalytic electrode of the present invention may have high power density, and thus has excellent physical properties.

Furthermore, the size of continuous pores is suitably controlled, and thus electrons produced in an enzyme can be relatively rapidly transferred to the inner surface of the continuous pores or can be transferred directly to the continuous pores. Thus, the catalytic electrode of the present invention may have high power density which was impossible in conventional enzyme electrodes, and thus has excellent physical properties.

In addition, the stability of enzymatic activity can be greatly improved compared to that of free enzymes by suitably controlling the structure and size of continuous pores and immobilizing an enzyme to the continuous pores using a method such as covalent bonding or post-adsorption crosslinking. The enzyme electrode of the present invention, which has stable and high enzymatic activity, ensures the durability of an enzyme electrode, which is problematic in enzymatic biosensors or biofuel cells, and thus it has excellent physical properties.

Therefore, the catalytic electrode of the present invention can be very efficiently used in fuel cells, biofuel cells, solar cells, secondary cells, supercapacitors and biosensors, as well as various fields in which catalytic electrodes are used.

BEST MODE FOR CARRYING OUT THE INVENTION

Hereinafter, the present invention will be described in further detail.

As described above, conventional catalytic electrodes prepared using Nafion have a problem in that Nafion greatly interferes with the transfer of electrons produced by a catalytic reaction to a current collector.

To solve the above problems, the present invention provides a method of preparing a catalytic electrode, the method comprising the steps of: (1) preparing a solution mixture including an electroconductive precursor, a pore support precursor and a continuous pore forming agent; (2) immersing an electrode support in the solution mixture to form a matrix filled in or coated on the electrode support; (3) calcining the matrix to remove the continuous pore forming agent and form continuous pores in the matrix; and (4) loading a catalyst into the continuous pores in the matrix.

In step (1), a solution mixture including an electroconductive precursor, a pore support precursor and a continuous pore forming agent is prepared. The electroconductive precursor that may be used in the present invention may be a precursor material that has electrical conductivity and, at the same time, can be coated or filled with an electrode support by calcination or the like. Preferably, the electroconductive precursor may include one or more precursor selected from the group consisting of a carbon precursor, a palladium precursor and a platinum precursor. More preferably, a carbon precursor may be used. A preferred carbon precursor that is used in the present invention may be one or more selected from the group consisting of resole, furfuryl alcohol, phenol-formaldehyde resin, resorcinol-formaldehyde resin, sucrose such as sugar, pitch and coal tar.

The pore support precursor will now be described. As used herein, the term "pore support precursor" refers to a material that is converted to a stable inorganic material in a high-temperature calcining process to increase the mechanical stability and thermal durability of a matrix. Further, the pore support precursor is uniformly distributed in the matrix so that it functions to prevent the collapse and shrinkage of pores in a high-temperature calcining process and to keep the pore stable and it functions like the framework of buildings. The electroconductive material is polymerized (high-temperature calcined or carbonized) around the pore support precursor as a framework so that the structure itself is kept stable, and as a result, the shape and size of continuous pores are kept stable. The pore support precursor that is used in the present invention may be a silicone alkoxide or an organosilicate such as tetraethyl orthosilicate (TEOS), tetramethyl orthosilicate (TMOS) or aluminosilicate.

Figure 4:
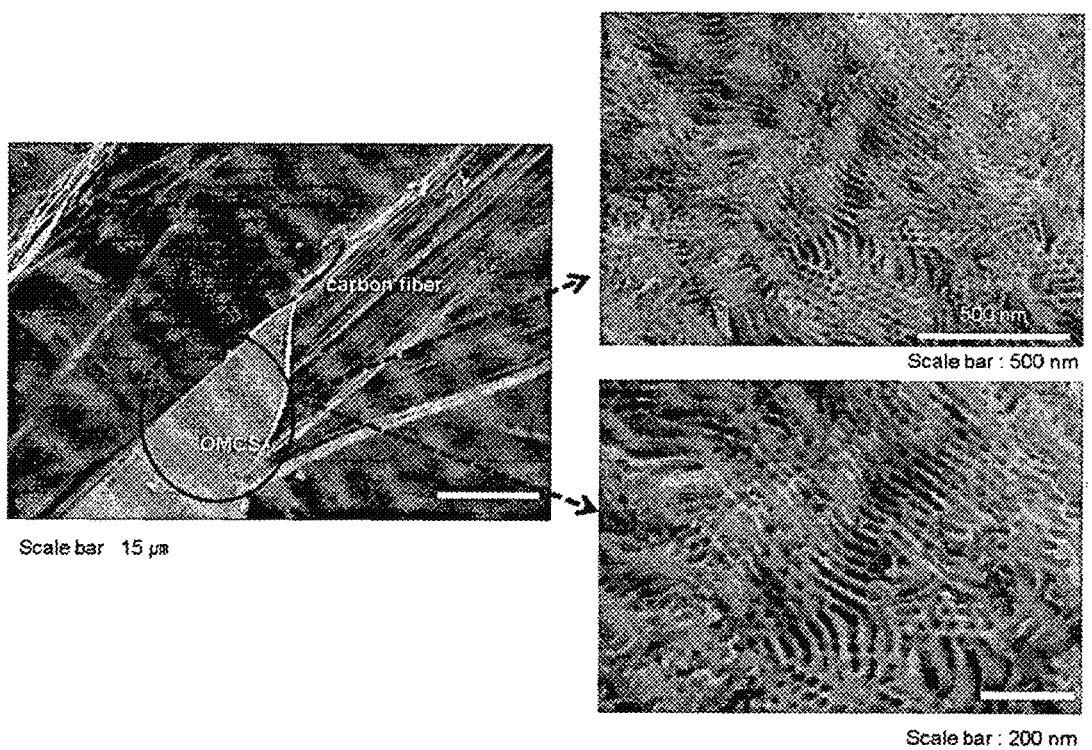
FIG. 4 is a SEM photograph of a continuous carbon-silica phase having continuous pores, which is formed on carbon fibers that constitute carbon paper according to a preferred embodiment of the present invention.

The continuous pore forming agent will now be described. As used herein, the term "continuous pore forming agent" refers to a material capable of forming continuous pores in the electroconductive material that is coated on or filled in the electrode support, and/or the pore support material. As used herein, the term "continuous pores" refers to a structure as shown in FIG. 4, in which pores are continuous without being clogged. Preferably, the continuous pore forming agent may be an amphiphilic block copolymer. The amphiphilic block copolymer has the property of being self-assembled into materials having various structures depending on the relative volume fraction (mass fraction) of each of the hydrophilic and hydrophobic blocks of the copolymer. The fraction of each of the blocks is controlled to form a thermodynamically most stable structure. When the volume fractions of the hydrophilic and hydrophobic parts are similar, a lamella structure is formed, and as the fraction of one of the blocks increases, various structures such as gyroid, hexagonal and cubic structures are formed. A phase as shown in FIG. 4, in which pores are continuous without being clogged, corresponds to a hexagonal structure. In the present invention, the formation of continuous pores was induced by artificially increasing the volume fraction of the hydrophilic part using a precursor that can be selectively injected only into the hydrophilic part of the amphiphilic block copolymer. As a result, the hydrophilic block of the amphiphilic block copolymer and the precursors formed a matrix, and the hydrophobic block was self-assembled into ordered pores to form continuous pores.

According to a preferred embodiment of the present invention, the amphiphilic block copolymer that is used in the present invention may have an ordered configuration in which the hydrophilic block and the hydrophobic block are covalently bonded to each other. In this case, the hydrophilic block may be one or more selected from the group consisting of polystyrene-b-poly(ethylene oxide), PS-b-PEO, polyisoprene-b-poly(ethlyene oxide), poly(ethylene oxide)-poly(propylene oxide)-poly(ethlyene oxide), poly(ethylene oxide), and poly(oligo(ethylene glycol)methacrylate) (POEGMA).

The hydrophobic block that is included in the amphiphilic block copolymer may be one or more selected from the group consisting of poly(styrene), poly(isoprene), and poly(methyl methacrylate).

Meanwhile, the average molecular weight of the amphiphilic block copolymer that is used in the present invention may range from 10,000 from 100,000, and the mass ratio of the hydrophilic block to the hydrophobic block may be 5:95 to 60:40.

According to another preferred embodiment of the present invention, the weight ratio of the continuous pore forming agent to the sum of the electroconductive material and the pore support precursor may be 1:3 to 1:6 or 1:1 to 4:1. Specifically, when the ratio of the block copolymer to the carbon precursor+the silica precursor is about 1:3 to 1:6 and the ratio of the carbon precursor to the silica precursor is about 1:1 to 4:1, continuous pores having a hexagonal channel shape may be formed. When the ratio of the precursors to the pore forming agent is 1:1 to 1:2, a lamellar structure will be formed, making it difficult to form pores, and when the ratio is 1:6 or more, a cubic structure will be formed, making it difficult to form continuous pores.

Meanwhile, the solvent of the solution mixture that is used in the present invention may be a solvent that has a function of uniformly dissolving all the electroconductive precursor, the pore support precursor and the continuous pore forming agent while having high volatility suitable for evaporation-induced self-assembly. Preferably, the solvent may be chloroform, tetrahydrofuran (THF), ethanol or the like.

Preferably, the solution mixture may include, based on 100 parts by weight of a solvent, 0.5-30 parts by weight of the electroconductive precursor, 0.5-30 parts by weight of the pore support precursor and 0.5-10 parts by weight of the continuous pore forming agent. If the content of the electroconductive precursor is less than 0.5 parts by weight, uniform coating of the electroconductive material will be difficult, and if the content is more than 30 parts by weight, it will interfere with pore formation by the continuous pore forming agent. If the content of the pore support precursor is less than 0.5 parts by weight, it cannot function to support pores in a high-temperature calcining process, and if the content is more than 30 parts by weight, it will interfere with pore formation by the continuous pore forming agent. If the content of the continuous pore forming agent is less than 0.5 parts by weight, it will be less than the concentration required for pore formation, and thus continuous pores will not be formed, and if the content is more than 10 parts by weight, it will not be self-assembled with the precursors, and phase separation will occur in which the continuous pore forming agent is present separately.

Meanwhile, the solution mixture may further include dimethyl-(1,5-cyclooctadiene)-platinum, triphenyl(phenylethynyl)lead, tributylphenyltin, triphenylantimony, ferrocene, nickelocene or cobaltocene, which is a hydrophobic precursor capable of interacting with the block copolymer.

Next, in step (2), the electrode support is immersed in the solution mixture to form a matrix filled in or coated on the electrode support. The electrode support that is used in the present invention may be any electrode support that may generally be used in catalytic electrodes. Preferably, the electrode support may be a carbon fibrous assembly or a silica structure. More preferably, it may be carbon paper, carbon felt or carbon cloth, which is widely used.

The electrode support is immersed in the solution mixture, prepared in step (1), for 10 seconds to 5 minutes, and is maintained at 20~50° C. for 120-720 minutes to form a matrix in which the electroconductive precursor, pore support precursor and continuous pore forming agent of the solution mixture are coated on and/or filled in the electrode support. The coated or filled matrix may be a hybrid composed of the electroconductive precursor, the pore support precursor and the continuous pore forming agent and may be in a partially polymerized form.

Next, in step (3), the matrix is calcined to remove the continuous pore forming agent and form continuous pores in the matrix. Preferably, the calcining process is performed at a temperature at which the continuous pore forming agent can be removed to form continuous pores in the matrix while the electroconductive material and the pore support material are not influenced. Preferably, the calcining process may be performed at 600~1000° C. for 120-600 minutes. In the calcining process, the self-assembled continuous pore forming agent is decomposed, and as a result, the matrix may include a plurality of continuous pores, and the electroconductive precursor and the pore support precursor are completely polymerized to form a continuous polymer phase.

The size of the continuous pores may be 1-1000 nm. Preferably, the size of the continuous pores may be suitably controlled depending on the size of a catalyst loaded in the continuous pores. The length of the continuous pores may depend on the size of the matrix and is not limited.

Meanwhile, the method of the present invention may further comprise, between steps (3) and (4), a step of removing the pore support material from the matrix. Removal of the pore support material may be performed using a known method according to the kind of pore support material. For example, when TEOS is used as the pore support material, it may be removed either by stirring in 1-2M NaOH solution at 100° C. for 2 hours or more or by stirring at 5-10 wt % of HF solution for 1 hour or more. When the pore support material is removed from the coated or filled matrix, various physical properties, including electrical conductivity, are significantly improved compared to when it is removed.

Further, when the pore support material is removed, some or all of the continuous pores in the matrix can be connected with each other, and as a result, the physical properties of the catalytic electrode are significantly improved. Silica is a material having a very low electrical conductivity, and if silica is present, the electrical conductivity of the catalytic electrode will be lowered. When silica is removed, pores corresponding to the size occupied by the silica will be newly formed. Depending on the particle size of removed silica, micropores having a size of 1 nm or less or mesopores having a size of 2 nm or more can additionally formed. Formation of additional pores increases the surface area and volume of the material. When silica is removed, numerous interconnecting pores that connect the continuous pores to each other are formed, and thus the electrical conductivity and stability of the catalytic electrode are significantly improved.

Next, in step (4), a catalyst is loaded into the continuous pores in the matrix. A catalyst that can be loaded into the continuous pores may be either an enzyme or a metal catalyst. When the catalyst is an enzyme, any enzyme may be used without limitation, as long as it is an enzyme that is generally used in enzymatic electrodes. Preferably, the enzyme may be one or more selected from the group consisting of glucose oxidase, glucose dehydrogenase, pyranose dehydrogenase, alcohol dehydrogenase, aldehyde dehydrogenase, formate dehydrogenase, diaphorase, microperoxidase-11, lactated dehydrogenase, hydrogenase, catalase, tyrosinase, laccase, cytochrome oxidase, soybean peroxidase, cytochrome c oxidase, chloroperoxidase, horseradish peroxidase, and bilirubin oxidase.

When the catalyst that is used in the present invention is a metal catalyst, any metal catalyst may be used without limitation, as long as it is a metal catalyst that can be generally used in catalytic electrodes. Preferably, the metal catalyst may be one or more selected from the group consisting of platinum, ruthenium, osmium, palladium, and alloys thereof. For example, as the metal catalyst that can be used in the present invention, the alloys may be selected from a platinum-ruthenium alloy, a platinum-osmium alloy, a platinum-palladium alloy, and a platinum-M alloy (wherein M is a transition metal selected from the group consisting of Ga, Ti, V, Cr, Mn, Fe, Co, Ni, Cu, Zn, Sn, Mo, W, Rh, Ru, and a combination thereof).

Specifically, for example, the alloys that can be used in the present invention may be selected from the group consisting of Pt, Pt/Ru, Pt/W, Pt/Ni, Pt/Sn, Pt/Mo, Pt/Pd, Pt/Fe, Pt/Cr, Pt/Co, Pt/Ru/W, Pt/Ru/Mo, Pt/Ru/V, Pt/Fe/Co, Pt/Ru/Rh/Ni, Pt/Ru/Sn/W, and a combination thereof.

The electrode structure fabricated through the above-mentioned method may include an electrode support; and an electroconductive material including continuous pores which are filled in or coated on the electrode support and is capable of being loaded with a catalyst.

As described above, the electroconductive material may include a composite of the electroconductive material such as carbon and the pore support material such as silica or may include the electroconductive material alone. The electroconductive material may include one or more materials selected from the group consisting of carbon, palladium, and platinum.

In addition, the electroconductive material filled in or coated on the electrode support includes continuous pores therein and may be in the form of a continuous phase composed of a polymer of the electroconductive material. As used herein, the term "continuous phase" refers to a continuous polymer phase rather than a shape such as power.

The kind of electrode support that may be used in the present invention is as described above. When the electrode support is a carbon fibrous assembly, the electroconductive material can fill the space between the carbon fibers and, at the same time, can coat the carbon fibers. Meanwhile, in a method of forming the interconnecting pores directly in a carbon support having a three-dimensional network structure, it is difficult to form standardized pores, and the size of the pores is also irregular. Thus, a catalyst cannot be efficiently loaded into the pores, and carbon fiber itself can be damaged, making the electrode itself unstable.

Further, when carbon paper or the like is coated with a conventional mesoporous carbon material, formed pores cannot be completely used to load a catalyst, and thus the efficiency with which the catalyst is loaded can be low, and the loaded catalyst is unstable because it cannot be kept stable in the pores. In addition, in order for electrons produced in the catalyst to be transferred smoothly, the pores of a material having electrically conductivity should be continuously connected with each other. However, the mesopores of conventional mesoporous carbon materials are mostly interparticle pores produced between carbon particles, and in this case, there is a disadvantage in terms of electron transfer because carbon particles are not sufficiently connected with each other.

The electroconductive material of the present invention includes continuous pores, and the diameter of the continuous pores can be suitably selected depending on the kind of catalyst. Preferably, the diameter of the continuous pores may be 1-1000 nm.

The electroconductive material of the present invention includes one or more continuous pores. More preferably, a plurality of continuous pores may be formed so that the porosity of the conductive material is 10-60%, and the continuous pores may be in an ordered form as shown in FIG. 4.

When some or all of the continuous pores are connected with each other, the loading and stability of the catalyst are increased.

In the meantime, according to a preferred embodiment of the present invention, there is provided a catalytic electrode including a catalyst in the continuous pores of the electrode support structure of the present invention. The catalyst may be either an enzyme or a metal catalyst.

If the electrode support is coated with conventional carbon ink or paste, there is a problem in that the carbon ink or paste is introduced into the pores of the porous carbon particles to reduce the loading of the catalyst or increase the mass transfer resistance of the electrode support.

However, because the catalytic electrode of the present invention has continuous pores formed therein, it can be loaded with a significantly large amount of a catalyst and has high stability, compared to conventional porous carbon particles. Further, because the electroconductive matrix (continuous phase) is well attached to the electrode support, an enzyme can be efficiently immobilized to the continuous pores using a method such as covalent bonding or post-adsorption crosslinking without having to use Nafion (perfluorinated sulfonic acid polymer). When an enzyme is immobilized to the continuous pores without using Nafion, the mass transfer resistance and electron transfer resistance by Nafion can be eliminated so that the catalytic electrode may have a very high power density.

The power density of the catalytic electrode is influenced by the production rate of electrons, which is determined by the loading amount of an enzyme, and the transfer rate of the produced electrons. Thus, a high enzyme loading can be realized by controlling the size of the continuous pores to a size that is greater than the enzyme, but is relatively small, to improve electron transfer, while a very high power density can be achieved by making electron transfer easy.

The average pore size of the continuous pores can be defined in various manners depending on the structure of the continuous pores or the standard deviation of the roughness of the inner surface or the pore size, but it may be 0.5-5 nm greater than the average diameter of the enzyme to ensure a high loading of the enzyme. Further, rapid electron transfer can be achieved by maintaining the average distance from the enzyme surface to the inner surface of the continuous pores at 10 nm or less, and in this case, electrons produced in the catalyst are not released to the outside of the continuous pores.

Particularly, it is difficult to realize the direct electron transfer of all the produced electrons, but 10% or more of the produced electrons can be transferred directly to the inner surface of the continuous pores. The remaining 90% of the electrons are more efficiently transferred to the continuous pores due to the high aspect ratio of the pores, compared to transfer to other various enzyme carriers.

Once electrons are transferred to the electroconductive matrix, these electrons are transferred directly or through the electroconductive electrode support to a current collector. Thus, the catalytic electrode of the present invention is a structure that maximizes electron transfer efficiency.

The loading amount of the catalyst is 10-100% of the total volume of pores capable of being loaded with the catalyst, and the power density per volume of the catalyst electrode can reach 250 μm/cm$^3$ or more.

The catalytic electrode of the present invention can be utilized for various purposes, and can be preferably used in fuel cells, biofuel cells, solar cells, secondary cells, and supercapacitors, biosensors, and the like.

EXAMPLES

Hereinafter, the present invention will be described in further detail with reference to examples. It will be obvious to a person having ordinary skill in the art that these examples are illustrative purposes only and are not to be construed to limit the scope of the present invention.

Preparation Example 1: Preparation of Carbon/Silica Composite (OMCS) Having Continuous Pores and Carbon (OMC)

Figure 2:
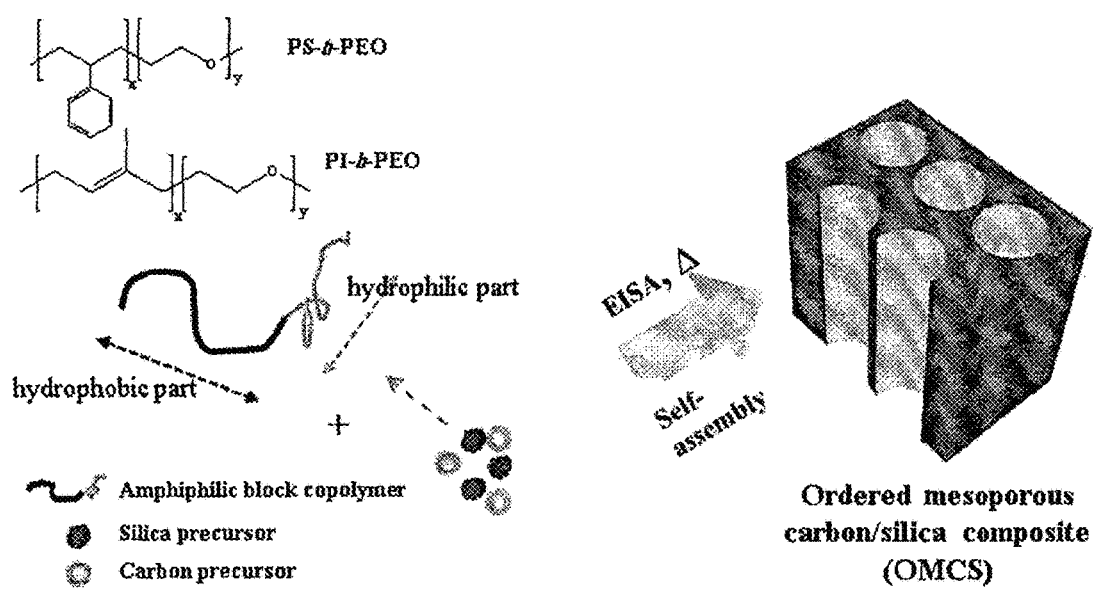
FIG. 2 is a schematic view showing a method of preparing a carbonaceous material having continuous pores according to a preferred embodiment of the present invention.

According to a method as shown in FIG. 2, a carbon/silica composite (OMCS) having continuous pores was prepared. Specifically, polystyrene-b-poly(ethylene oxide) (PSb-PEO) that is an amphiphilic block copolymer represented by the following formula 1 was used as a structure directing agent for forming continuous pores in the composite and dissolved in the organic solvent chloroform. 15 g of the amphiphilic block copolymer was mixed with 6 ml of chloroform.

The total molecular weight of the amphiphilic block copolymer used was 29,000, the molecular weight of the polyethylene oxide (PEO) was 5000 (17.2%), the PDI (polydispersity index) was 1.09, and the molar ratio of the monomers was PS:PEO=0.64:0.36.

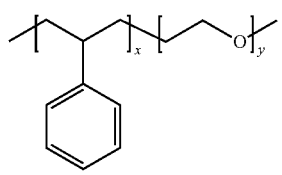

[Formula 1]

PS-b-PEO wherein x is 203, and y is 113.

Then, a silica precursor (TEOS, 0.426 ml), 0.1 M HCl (0.045 ml) and 0.22 g of a carbon precursor represented by the following formula 2 were sequentially added to chloroform and stirred at room temperature for 1 hour to prepare a precursor solution. The precursor solution was cast into a Petri dish. The organic solvent was evaporated by an evaporation-induced self-assembly (EISA) process and, at same time, the concentration of the mixture increased while the copolymer was self-assembled. Due to the self-assembly of the amphiphilic block copolymer, an ordered nanophase was formed. Then, the mixture was subjected to an annealing process for 24 hours at 100° C., and thus the silica and carbon precursors started to form the respective structural networks, and the mixture was solidified. To obtain OMCS, the mixture was finally calcined at 800° C. As the temperature increased, hard silica and carbon supports were formed, and polystyrene from the block copolymer was decomposed to form pores having a size of about 20 nm. At the same time, polyethylene from the block copolymer attached to the carbon-silica wall was also decomposed to form micropores having a size of 1 nm or less. The resulting material had an ordered 2-D hexagonal type structure, a pore size of about 20 nm and a wall thickness of about 10 nm between the pores, and the thickness of the resulting carbon/silica composite (OMCS) having continuous pores was about 1 μm.

Silica was selectively removed from the prepared OMCS to prepare OMC. Specifically, OMCS was immersed in an aqueous solution of 1M NaOH, and then stirred at 100° C. for 2 hours, and the stirred solution was washed several times with distilled water, and then dried in a drying oven at 100° C. for 12 hours, thereby preparing OMC.

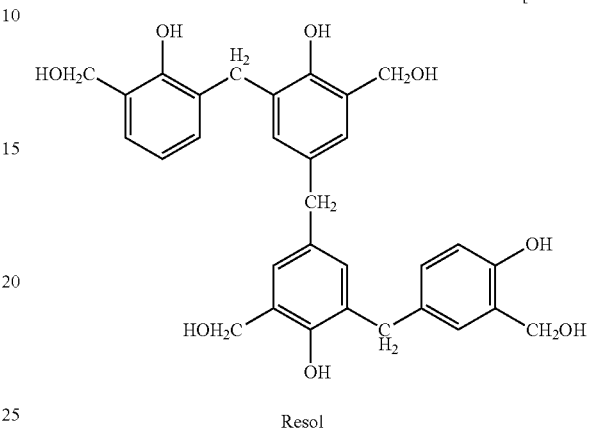

[Formula 2]

Resol

The IUPAC name of resole that is the carbon precursor of Formula 2 is 4,6'-(5,5'-methylenebis(2-hydroxy-3-(hydroxymethyl)-5,1-phenylene))bis(methylene)bis(2-(hydroxymethyl)phenol).

Process of examining the structural ordering, surface area, pore volume, pore size and pore shape of the material prepared using the block copolymer and the silica and carbon precursors having continuous pores. Polystyrene-b-poly(ethylene oxide) (PS-b-PEO) that is an amphiphilic block copolymer is used as a structure directing agent. The size of the formed pores is in the range of 15 to 50 nm and determined by the molecular weight of the block copolymer used, and the molecular weight of the copolymer used may be in the range of 10,000 to 100,000. The shape of the pores is determined by the volume ratio of the hydrophobic part (polystyrene) and hydrophilic part (poly(ethylene oxide)) of the amphiphilic block copolymer, the silica precursor and the carbon precursor. When the ratio of the hydrophobic part to the hydrophilic part is in the range of 1:3 to 1:5, a 2-dimensional hexagonal type (continuous pore) structure can be formed. The formation and ordering of the structure are determined by the following two conditions. The first condition is the polydispersity index (PDI) of the amphiphilic block copolymer used as the structure directing agent. As the polydispersity index approaches 1, the molecular weight is uniform, and the ordering of the structure is high. The second condition is the miscibility between the block copolymer and silica and between the clock copolymer and the carbon precursor. If the miscibility is low, the structure is not formed, because phase separation occurs during the self-assembly of the materials. In order to increase the miscibility, the silica and carbon precursors used should have a size smaller than the poly(ethylene oxide) chain length of the block copolymer and should have chemical affinity. Tetraethyl orthosilicate or aluminosilicate used as the silica precursor in the present invention, and furfuryl alcohol or resole used as the carbon precursor have a suitable size of 5 nm or less. Further these precursors are rich in hydroxyl groups (—OH), and thus greatly interact with the ethylene oxide of the block copolymer by hydrogen bonding. The ratio of silica to carbon is a factor that determines the mechanical stability of the resulting mesoporous material. If the ratio of the silica precursor is 20% or less, the shrinkage of the structure during the high-temperature heat treatment process, and the resulting collapse of the structure and the blocking of the pores will occur. In the present invention, the ratio of silica to carbon was controlled to 1:1 to 1:10, and a silica-to-carbon ratio of 1:1 was found to be the most optimized condition.

Preparation Example 2: Preparation of Carbon Paper (CP), OMCS-CP and OMC-CP Coated with OMCS and OMC Having Continuous Pores Polystyrene-b-poly(ethylene oxide) (PS-b-PEO) that is an amphiphilic block copolymer represented by Formula 1 as described in Preparation Example 1 was used as a structure directing agent for forming continuous pores in the composite and dissolved in the organic solvent chloroform. 0.15 g of the amphiphilic block copolymer was mixed with 6 ml of chloroform.

The total molecular weight of the amphiphilic block copolymer used was 29,000, the molecular weight of the polyethylene oxide (PEO) was 5000 (17.2%), the PDI (polydispersity index) was 1.09, and the molar ratio of the monomers was PS:PEO=0.64:0.36. A carbon paper electrode (CP) (Fuel Cell Store, San Diego, Calif., USA) having a thickness of 370 µm and an area of 0.332 $cm^2$ was used.

Then, a silica precursor (TEOS, 0.426 ml), 0.1 M HCl (0.045 ml) and 0.22 g of the carbon precursor represented by formula 2 were sequentially added to chloroform and stirred at room temperature for 1 hour to prepare a precursor solution. Then, the carbon paper was immersed in the precursor solution for 5 minutes, and then transferred into a Petri dish. The precursor solution was subjected to an evaporation-induced self-assembly (EISA) process, and in this process, the organic solvent was evaporated, and the concentration of the mixture increased while the copolymer was self-assembled. Due to the self-assembly of the amphiphilic block copolymer, an ordered nanophase was formed. Then, the mixture was subjected to an annealing process for 24 hours at 100° C., and thus the silica and carbon precursors started to form the respective structural networks, and the mixture was solidified. To obtain OMCS-CP, the material annealed at 100° C. for 244 hours was calcined (carbonized) at 800° C. As the temperature increased, the annealed mixture was converted into hard silica and carbon supports, and polystyrene from the block copolymer was decomposed to form pores having a size of about 20 nm. At the same time, polyethylene from the block copolymer attached to the carbon-silica wall was also decomposed to form micropores having a size of 1 nm or less. The resulting material had an ordered 2-D hexagonal type structure, a pore size of about 20 nm and a wall thickness of about 10 nm between the pores.

Silica was selectively removed from the prepared OMCS-CP to prepare OMC-CP. Specifically, OMCS-CP was immersed in an aqueous solution of 1M NaOH, and then stirred at 100° C. for 2 hours, and the stirred solution was washed several times with distilled water, and then dried in a drying oven at 100° C. for 12 hours, thereby preparing OMC-CP.

Example 1: Fabrication of ADS-GOx/OMCS-CP Electrode

Figure 3:
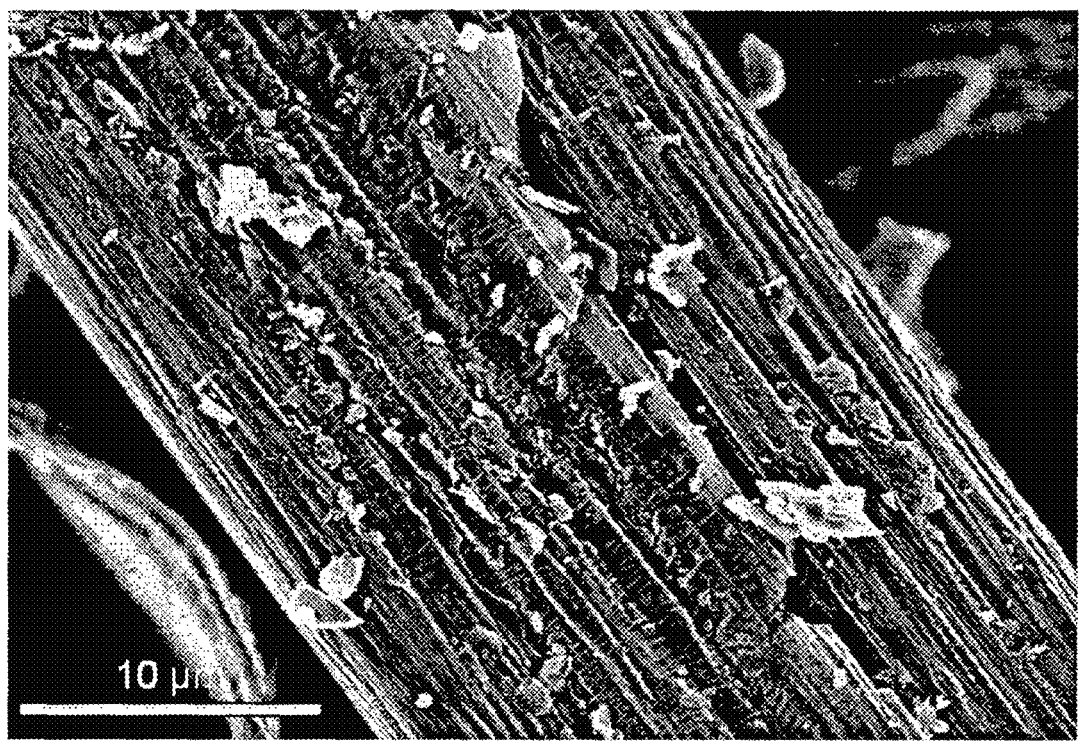
FIG. 3 is a scanning electron microscope (SEM) photograph of micrometer-sized carbon fibers that constitute carbon paper on which an electrode is based.

Carbon paper (see FIG. 3) was immersed in the precursor mixture solution (OMCS precursor solution) prepared in Preparation Example 2. A carbon paper electrode (CP) (Fuel Cell Store, San Diego, Calif., USA) having a thickness of 370 µm and an area of 0.332 $cm^2$ was used. After the solvent was evaporated at room temperature, the same procedure was repeated once more, whereby the space between the carbon fibers of the carbon paper was filled again with the OMCS precursor solution. The organic solvent was evaporated by the EISA process while the OMCS precursor material was coated on the surface of the carbon fibers. Then, the resulting material was subjected to a calcining process in the same manner as described in Preparation Example 1, thereby fabricating carbon fibers (OMCS-CP) filled/coated with the carbon/silica composite. FIG. 4 is a SEM photograph of OMCS—CP, and the right photographs of FIG. 4 are enlarged photographs of OMCS-CP. As can be seen therein, the surface of carbon fibers was coated with an OMCS layer, and the OMCS layer formed continuous pores like a honeycomb shape.

Next, OMCS-CP was added to 10 mg/ml of glucose oxidase (GOx), and then stirred at 100 rpm for 1 hour so that the enzyme could be loaded well into the continuous pores. Then, the resulting material was allowed to react at 4° C. for 12 hours so that the enzyme could be stably loaded into the continuous pores of the carbon electrode, after which it was washed several times with 100 mM PB buffer, thereby fabricating an ADS-GOx/OMCS-CP enzyme electrode which does not comprise Nafion which was necessarily used in the fabrication of conventional enzyme electrodes.

Example 2: Fabrication of ADS-GOx/OMC-CP Electrode (Silica Removal Process)

Figure 5:
FIG. 5 is a SEM photograph of a continuous carbon phase and portions coming into contact therewith, which are formed on carbon fibers that constitute carbon paper according to a preferred embodiment of the present invention.
Figure 6:
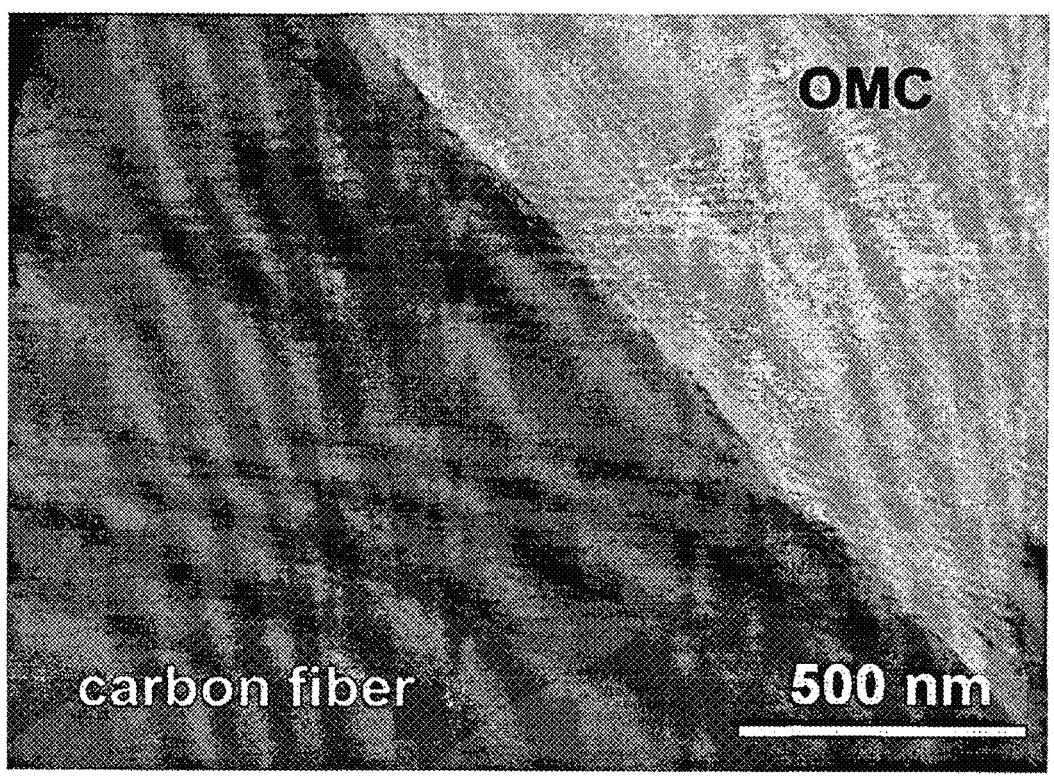
FIG. 6 is a transmission electron microscope (TEM) photograph showing that carbon fibers that constitute carbon paper are connected directly with a continuous carbon phase having continuous pores according to a preferred embodiment of the present invention.

Silica was selectively removed from the OMCS-CP electrode fabricated in Example 1, thereby fabricating the OMC-CP electrode shown in FIG. 5. Specifically, the OMCS-CP electrode was immersed in an aqueous solution of 1M NaOH, stirred at 100° C. for 2 hours, washed several times with distilled water, and then dried at a drying oven at 100° C. for 12 hours, thereby fabricating an OMC-CP electrode.

Next, OMCS-CP was added to 10 mg/ml of glucose oxidase (GOx), and then stirred at 100 rpm for 1 hour so that the enzyme could be loaded well into the continuous pores. Then, the resulting material was allowed to react at 4° C. for 12 hours so that the enzyme could be stably loaded into the continuous pores of the carbon electrode, after which it was washed several times with 100 mM PB buffer, thereby fabricating an ADS-GOx/OMCS-CP enzyme electrode which does not comprise Nafion which was necessarily used in the fabrication of conventional enzyme electrodes.

Comparative Example 1: Fabrication of Enzyme Electrode Having No Continuous Pore by Formation of Functional Group by Surface Modification of Carbon Paper (on which the Electrode is Based) and Covalent Attachment (CA) of the Functional Group to Enzyme A carbon paper electrode (CP) (Fuel Cell Store, San Diego, Calif., USA) having a thickness of 370 µm and an area of 0.332 $cm^2$ was used. The carbon paper having no functional group was added to a solution mixture of sulfuric acid and nitric acid (3:1 v/v) and stirred for 12 hours to form a carboxyl group on the surface of the carbon fibers of the carbon paper. Then, the carbon paper was treated with EDC-NHS in 100 mM MES buffer (pH 6.5), after which it was added to 10 mg/ml of GOx solution and stirred at room temperature at 100 rpm for 1 hour. Next, the resulting material was allowed to sufficiently react at 4° C. for 12 hours, and then washed several times with 100 mM PB buffer to remove the leaked enzyme. The formed CA-GOx/CP enzyme electrode was stored at 4° C. until use.

Comparative Example 2: Fabrication of Enzyme Electrode Having Continuous Pores Using Nafion Used Conventionally after Loading of Enzyme into OMCS OMCS prepared in Preparation Example 1 washed with water, after which it was mixed with 10 mg/ml of GOx solution and then stirred at 100 rpm for 1 hour so that GOx could be loaded well into the pores of OMCS. Following this, the resulting material was allowed to react at 4° C. for 12 hours so that the enzyme could be sufficiently stably loaded, after which it was allowed to react at 4° C. for 12 hours and washed several times with 100 mM PB buffer, thereby forming ADS-GOx/OMCS.

A carbon paper electrode (CP) (Fuel Cell Store, San Diego, Calif., USA) having a thickness of 370 μm and an area of 0.332 cm$^2$ was used. For hydrophilicity, the carbon paper was added to a solution mixture of sulfuric acid and nitric acid (3:1 v/v) and stirred for 12 hours, followed by washing. 5% Nafion solution was added to 25 mg/ml of a solution of ADS-GOx/OMCS so that the Nafion concentration of the solution was 0.5%. Then, the mixture was allowed to react at 4° C. for 1 hour while it was stirred so that the Nafion solution could be mixed well with the ADS-GOx/OMCS solution. The prepared carbon paper was added to the reacted solution so that the solution was adsorbed well onto the surface of the carbon paper. For stable adsorption of the solution onto the carbon paper, the carbon paper was kept in the solution at room temperature for 10 minutes, and then dried at room temperature for 1 hour. After drying, the resulting material was washed several times with 100 mM PB buffer, thereby forming an ADS-GOx/OMCS enzyme electrode which was then stored in 100 mM PB buffer at 4° C.

Comparative Example 3: Fabrication of Enzyme Electrode Having Continuous Pores Using Nafion Used Conventionally after Loading of Enzyme into Ordered Mesoporous Carbon Materials (OMC)

OMCS prepared in Preparation Example 1 washed with water, after which it was mixed with 10 mg/ml of GOx solution and then stirred at 100 rpm for 1 hour so that GOx could be loaded well into the pores of OMCS. Following this, the resulting material was allowed to react at 4° C. for 12 hours so that the enzyme could be sufficiently stably loaded, after which it was allowed to react at 4° C. for 12 hours and washed several times with 100 mM PB buffer, thereby forming ADS-GOx/OMCS.

A carbon paper electrode (CP) (Fuel Cell Store, San Diego, Calif., USA) having a thickness of 370 μm and an area of 0.332 cm$^2$ was used. For hydrophilicity, the carbon paper was added to a solution mixture of sulfuric acid and nitric acid (3:1 v/v) and stirred for 12 hours, followed by washing. 5% Nafion solution was added to 25 mg/ml of a solution of ADS-GOx/OMCS so that the Nafion concentration of the solution was 0.5%. Then, the mixture was allowed to react at 4° C. for 1 hour while it was stirred so that the Nafion solution could be mixed well with the ADS-GOx/OMCS solution. The prepared carbon paper was added to the reacted solution so that the solution was adsorbed well onto the surface of the carbon paper. For stable adsorption of the solution onto the carbon paper, the carbon paper was kept in the solution at room temperature for 10 minutes, and then dried at room temperature for 1 hour. After drying, the resulting material was washed several times with 100 mM PB buffer, thereby forming an ADS-GOx/OMCS enzyme electrode which was then stored in 100 mM PB buffer at 4° C.

Comparative Example 4: Fabrication of Enzyme Electrode by Addition of Nafion Solution after Loading of Enzyme into OMCS-CP OMCS-CP prepared in Example 1 was added to 10 mg/ml of GOx solution and stirred at 100 rpm for 1 hour, after which the mixture was allowed to react at 4° C. for 12 hours so that the enzyme could be sufficiently stably loaded. The reacted material was washed several times with 100 mM PB buffer, thereby forming ADS-GOx/OMCS-CP which was then stored in 100 mM PB buffer. Next, a Nafion solution was added thereto so that the final Nafion concentration was 0.5%, thereby forming an ADS-GOx/OMCS-CP nafion enzyme electrode.

Figure 1:
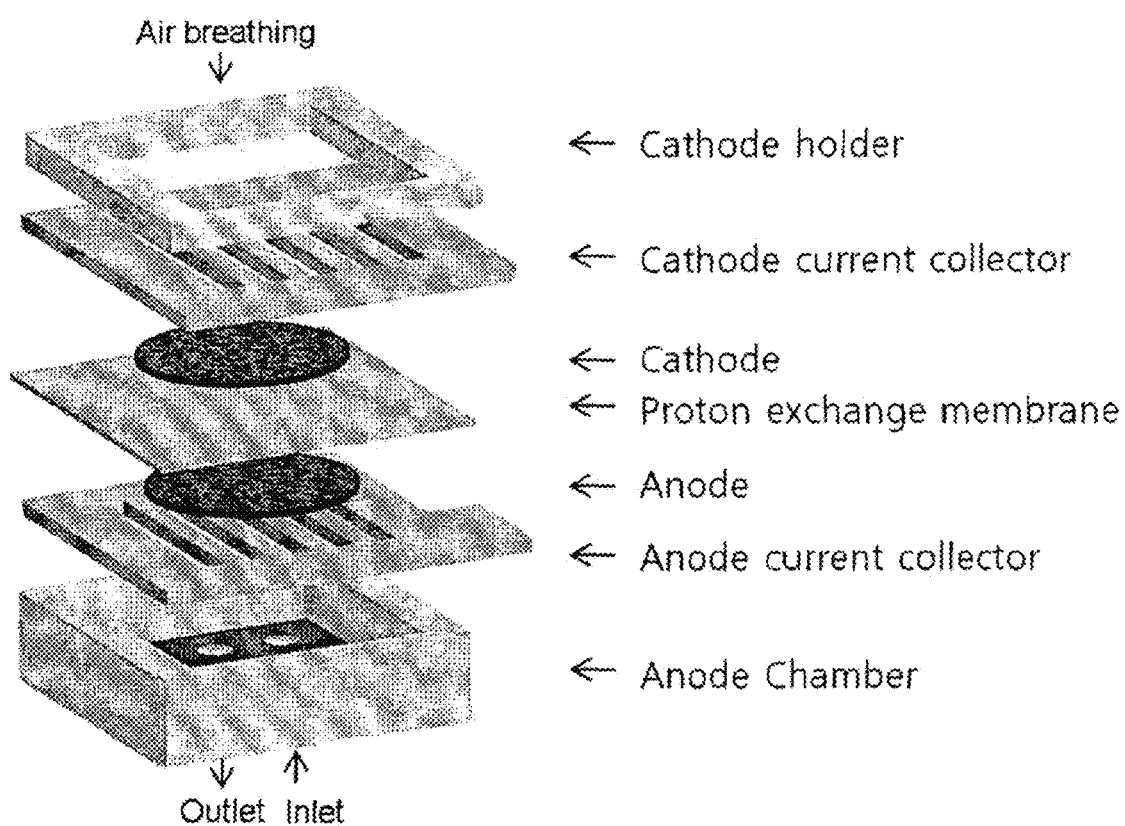
FIG. 1 is an exploded perspective view schematically showing a conventional biofuel cell.

Example 3: Fabrication of Biofuel Cells and Measurement of Polarization Curves and Maximum Densities The enzyme electrodes fabricated in Examples 1 and 2 and Comparative Examples 1 to 4 were used as cathodes, thereby fabricating fuel cells having a biofuel cell configuration as shown in FIG. 1. Specifically, each of the fuel cells was composed of an enzymatic cathode comprising the enzymatic electrode based on carbon paper, a cathode space, a current collector and a membrane electrode assembly (MEA). A proton exchange membrane, an air pump and a Pt anode electrode were purchased from Fuel Cell Store (San Diego, Calif., USA). To measure the performance of the biofuel cells, 200 mM glucose solution was fed into the biofuel cells by the pump at a rate of 0.6 ml/min, and a sufficient amount of air was fed to the anode. Using the constant load discharge (CLD) mode of Bio-Logic SP-150 that is an electrochemical analysis system, the polarization curves could be obtained and the maximum power densities could be calculated therefrom. The CLD mode was set such that specific external resistance to the biofuel cells was changed at intervals of 3 minutes, and the polarization curves (see FIG. 7) were obtained from the resulting changes in voltage and current, and the maximum current densities were calculated based on the curves.

Example 4: Measurement of Stability of Enzyme Electrode of Biofuel Cell

The enzyme electrode of Example 2 was stored at 4° C., and after 300 days, the maximum power density was examined in the same manner as described in Example 3. In addition, while the enzyme electrode of Example 2 was stored at room temperature, the maximum power density was examined once at intervals of several days to demonstrate the stability.

Example 5: Improvement in Performance of Enzyme Electrode of Biofuel Cell 1-7 enzyme electrodes of Example 2 were stacked, and the maximum power density of the biofuel was measured. As a result, it was shown that the maximum power density increased in proportion to the number of the electrodes, suggesting that the output of the biofuel cell was improved. To measure the performance of the enzyme electrode of the biofuel cell, the maximum power density was measured by obtaining the polarization curve using 200 mM glucose solution as a fuel (see FIG. 7 and Table 1).

TABLE 1

| | Maximum power density ($\mu W/cm^2$) |
|---|---|
| Comparative Example 1 (CA-GOx/CP) | 6.00 ± 0.23 |
| Comparative Example 2 (ADS-GOx/OMCS_nafion) | 9.09 ± 0.92 |
| Comparative Example 3 (ADS-GOx/OMC_nafion) | 11.62 ± 1.33 |
| Comparative Example 4 (ADS-GOx/OMCS-CP_nafion) | 12.83 ± 0.97 |
| Example 1 (ADS-GOx/OMCS-CP) | 21.40 ± 1.33 |
| Example 2 (ADS-GOx/OMC-CP) | 28.19 ± 0.38 |

Figure 7:
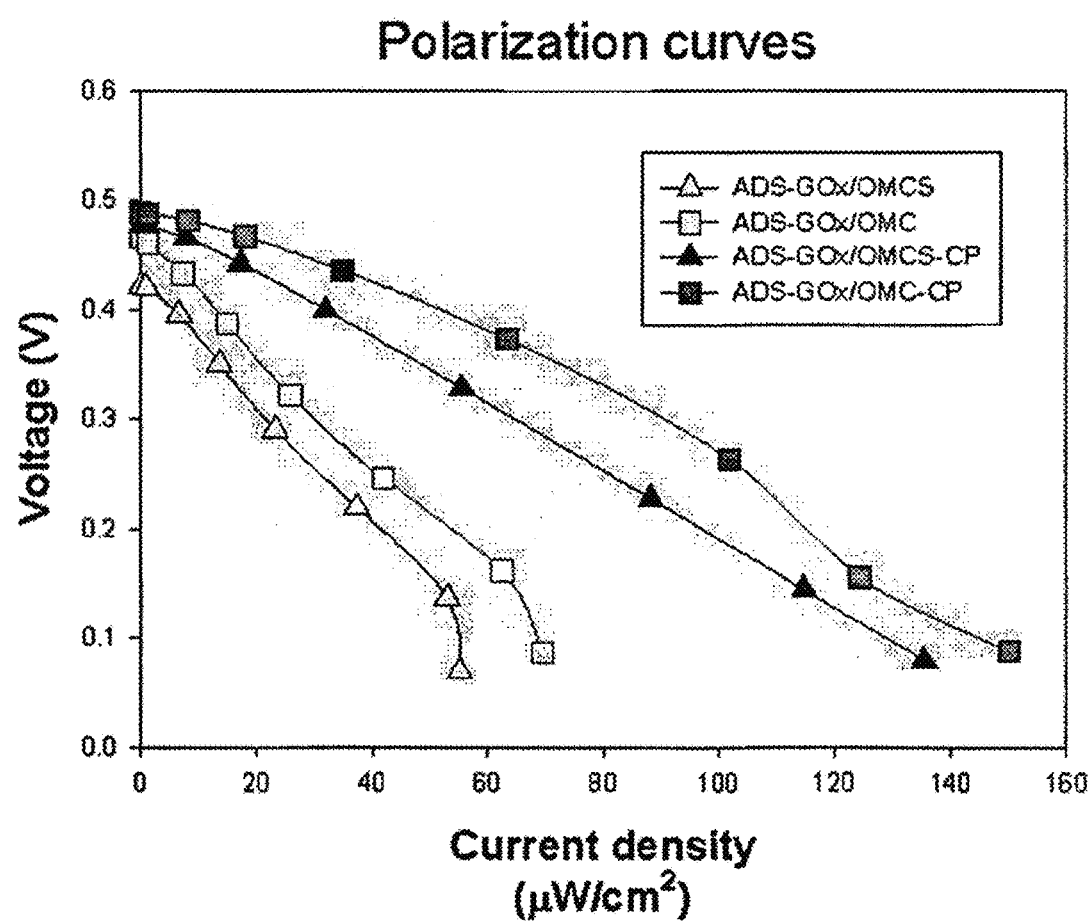
FIG. 7 shows polarization curves of biofuel cells.

As can be seen in FIG. 7 and Table 1, the maximum power density of the enzyme electrode of Example 1 in which no Nafion membrane was used was 2-4 times higher than those of Comparative Examples 2 and 4 in which the Nafion membrane was used, and Comparative Example 1 in which only simple covalent attachment was performed.

This suggests that, as a result of the development of the electrode having continuous pores, Nafion is not used so that electron transfer resistance by Nafion is eliminated, and thus the electron transfer efficiency of the electrode is increased and the performance thereof is improved.

As can be seen in FIG. 7 and Table 1, the maximum power density of the enzyme electrode of Example 1 in which no Nafion membrane was used was about two times higher than that of Comparative Example 4 in which the enzyme electrode was fabricated with the same material according to the same method using the Nafion membrane, suggesting that this increase in the maximum power density is attributable to the decrease in mass transfer resistance and that the performance of the electrode is improved because the Nafion membrane is not used.

In addition, it can be seen that the maximum power density of the enzyme electrode of Example 2 was 2-5 times higher than those of Comparative Examples 1 to 4 and 1.3 times higher than that of Example 1. This suggests that electron transfer resistance by silica is eliminated by removing silica from the carbon electrode, and thus the electron transfer efficiency of the electrode is increased and the performance thereof is improved.

Figure 8:
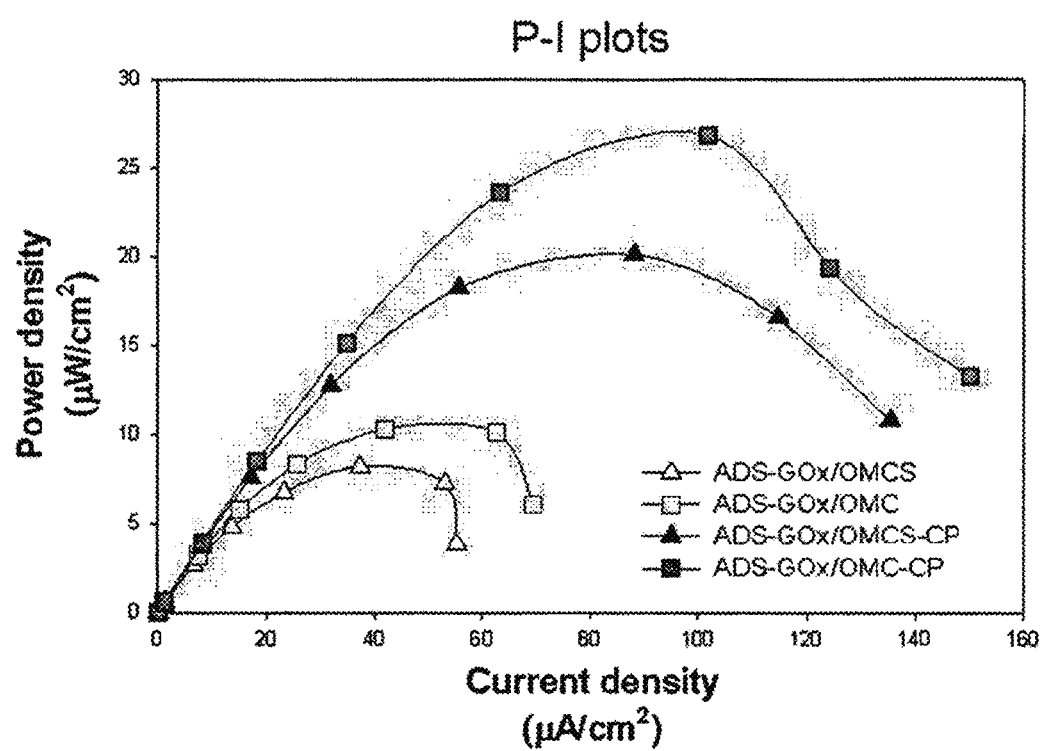
FIG. 8 is a graphic diagram showing the maximum power densities of biofuel cells.
Figure 9:
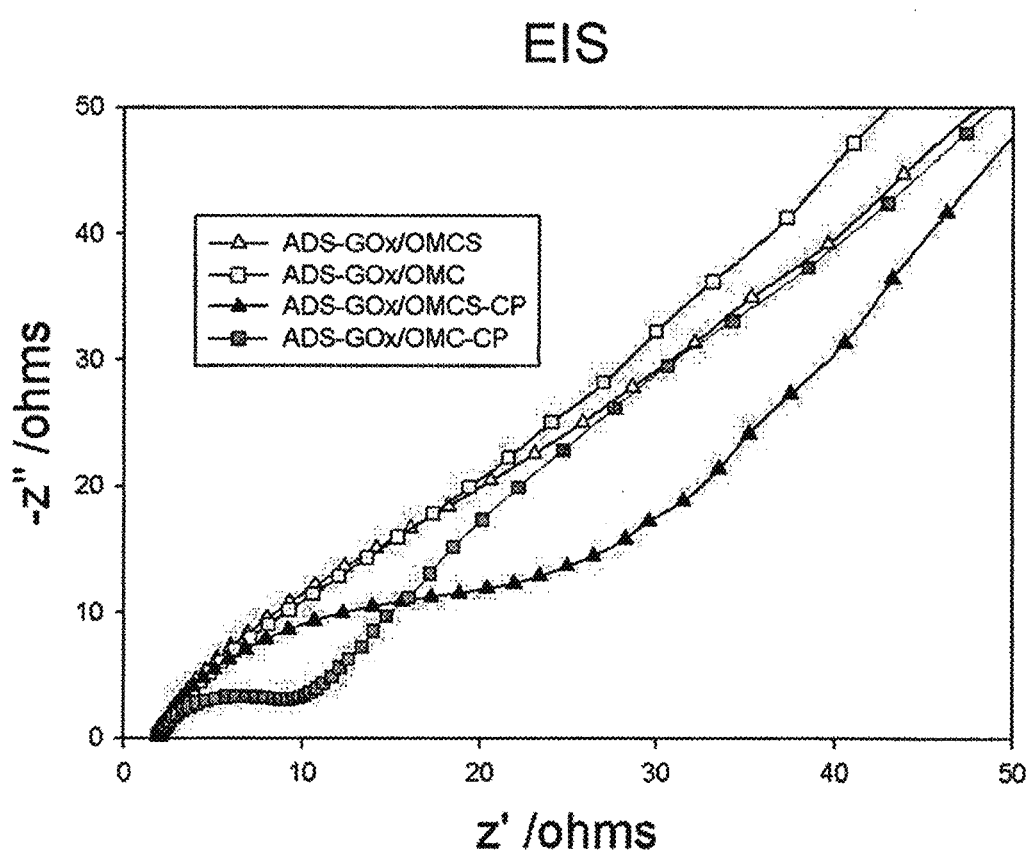
FIG. 9 is a graphic diagram showing the results of electrochemical impedance spectroscopy (EIS) of biofuel cells.

As can be seen in FIG. 8, the electron transfer resistance of the enzyme electrode of Example 2 was 2-3 times lower than those of Comparative Examples 2 and 3, and the electron transfer resistance of the enzyme electrode of Example 1 was 2-3 times lower than that of Example 3, suggesting that the increase in the maximum power density is attributable to the decrease in the electron transfer resistance. FIG. 9 shows the relationship between maximum power density and electron transfer resistance, and as can be seen therein, the maximum power density increases as the electron transfer resistance decreases.

Figure 10:
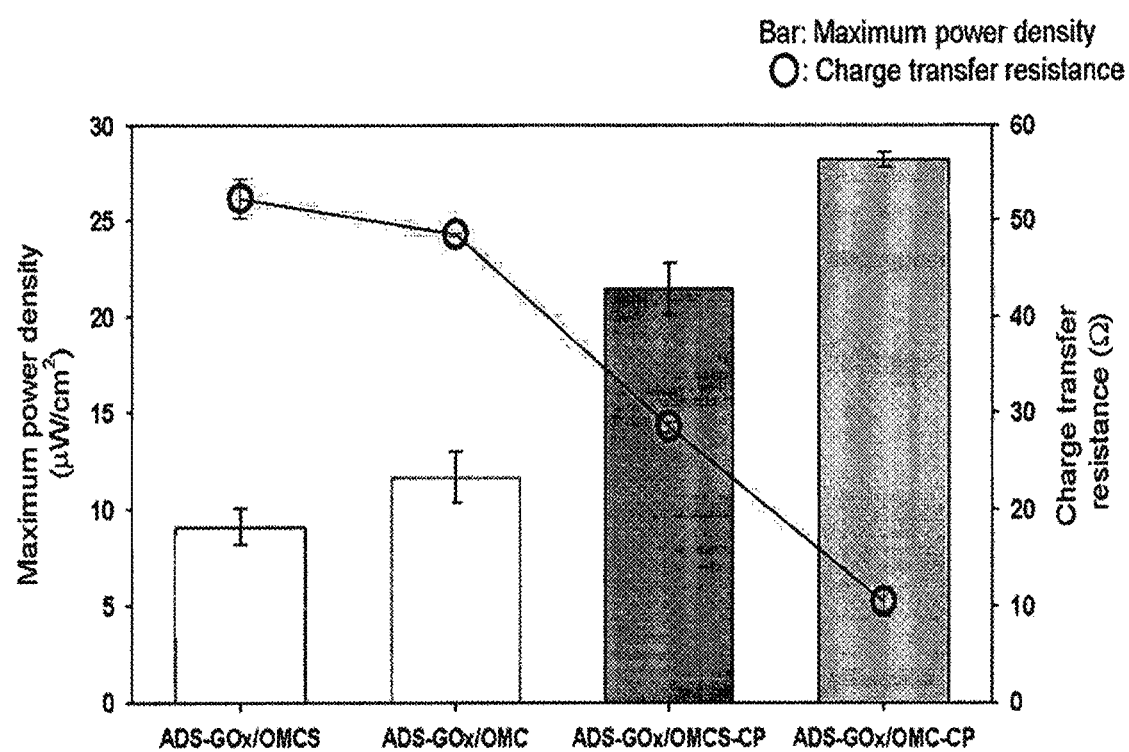
FIG. 10 is a graphic diagram showing the relationship between the maximum power density and charge transfer resistance of biofuel cells.

As can be seen in FIG. 10, when several electrodes of Example 2 were stacked in order to increase the maximum power density of the biofuel cell, the maximum power density increased in proportion to the number of the electrodes. This suggests that the electrode is highly applicable to the field in which high power can be required.

Figure 12:
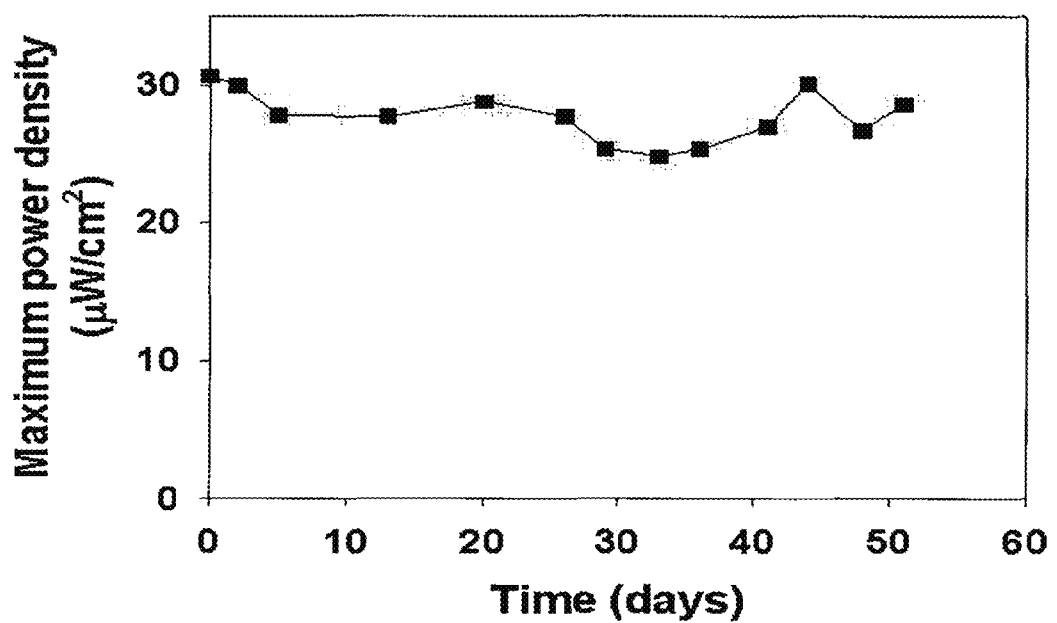
FIG. 12 is a graphic diagram showing the stability of a biofuel cell of Example 2.

To examine the stability of the enzyme electrode of the biofuel, the maximum power densities were measured by obtaining the polarization curves of the enzyme electrodes of Examples 1 and 2 (stored at room temperature and 4° C.) using 200 mM glucose solution as a fuel (see FIG. 12 and Table 2).

TABLE 2

| Storage condition (4) | Maximum power density ($\mu W/cm^2$) | |
|---|---|---|
| Days | 0 | 293 |
| Example 1 (ADS-GOx/OMCS-CP) | 20.07 | 23.19 |
| Example 2 (ADS-GOx/OMC-CP) | 27.81 | 30.83 |

As can be seen in FIG. 12, the maximum power density of the biofuel cell of Example 2 was maintained for 30 days or more at room temperature without change. In addition, as can be seen in Table 2, the maximum power densities of the biofuel cells of Examples 1 and 2 were maintained for 300 days at 4° C. without a decrease in the performance. This suggests that the unstable enzyme was stabilized by adsorption into the pores of the carbon polymer (continuous phase) having continuous pores and that the lifespan of the biofuel cells was increased.

Figure 11:
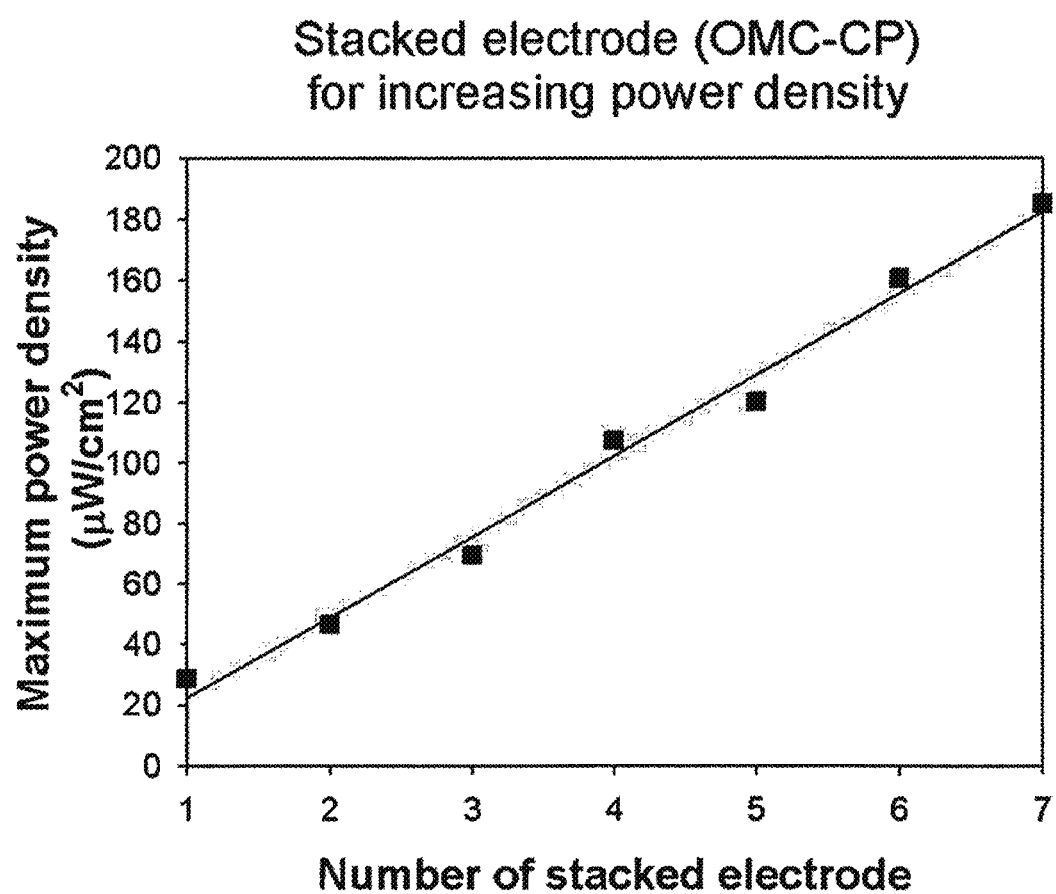
FIG. 11 is a graphic diagram showing the results of stacking several electrodes in order to increase the power density of a biofuel cell of Example 2 and measuring an increase in the maximum power density.

The results shown in FIGS. 11 and 12 suggest that the electrode of the present invention can become a solution to a low output and a short lifespan, which are the greatest limits to the actual application of biofuel cells.

INDUSTRIAL APPLICABILITY

The catalytic electrode of the present invention can be widely used in fuel cells, biofuel cells, secondary cells, supercapacitors and biosensors, as well as various fields in which catalytic electrodes can be used.

The invention claimed is:

1. A catalytic electrode structure, comprising an electrode support, and a porous continuous electroconductive material on the electrode support in direct contact therewith, with no binder binding the porous continuous electroconductive material onto the electrode support, wherein the porous continuous electroconductive material comprises pores whose diameters are within a range of 1 to 1000 nm, and wherein at least some of the pores are connected with each other.

2. The catalytic electrode structure of claim 1, wherein the electrode support is either a carbon fibrous assembly or a silica structure.

3. The catalytic electrode structure of claim 1, wherein a catalyst comprising at least one enzyme or metal catalyst is present in pores of the porous continuous electroconductive material.

4. The catalytic electrode structure of claim 1, wherein an immobilized catalyst is at least one of covalently bonded, adsorbed, and cross-linked in pores of the porous continuous electroconductive material.

5. A cell comprising the catalytic electrode structure of claim 1.

6. The cell of claim 5, wherein the cell is one selected from the group consisting of a fuel cell, a biofuel cell, a solar cell, a secondary cell, and a supercapacitor.

7. A biosensor comprising the catalytic electrode structure of claim 1.

8. A method of preparing a catalytic electrode structure, the method comprising: (1) preparing a solution mixture comprising an electroconductive precursor, a pore support precursor, and a continuous pore forming agent; (2) immersing an electrode support in the solution mixture thereby forming a continuous electroconductive material on the electrode support in direct contact therewith; (3) calcining the continuous electroconductive material to remove the continuous pore forming agent thereby forming continuous pores in the continuous electroconductive material, to provide a porous continuous electroconductive material on the electrode support in direct contact therewith, wherein the porous continuous electroconductive material comprises pores whose diameters are within a range of 1 to 1000 nm, and wherein at least some of the pores are connected with each other, with no binder binding the porous continuous electroconductive material onto the electrode support; and (4) loading a catalyst into the continuous pores in the porous continuous electroconductive material on the electrode support.

9. The method of claim 8, wherein the electroconductive precursor comprises one or more precursors selected from the group consisting of a carbon precursor, a palladium precursor, and a platinum precursor.

10. The method of claim 9, wherein the carbon precursor is one or more selected from the group consisting of resole, furfuryl alcohol, phenol-formaldehyde resin, resorcinol-formaldehyde resin, sucrose, pitch, and coal tar.

11. The method of claim 8, wherein the pore support precursor is silicone alkoxide or organosilicate, the continuous pore forming agent is an amphiphilic block copolymer, and the electrode support is a carbon fibrous assembly or a silica structure.

12. The method of claim 11, wherein the amphiphilic block copolymer comprises a hydrophilic block and a hydrophobic block, wherein the hydrophilic block is one or more selected from the group consisting of polystyrene-b-poly(ethylene oxide)(PS-b-PEO), polyisoprene-b-poly(ethlyene oxide), poly(ethylene oxide)-poly(propylene oxide)-poly(ethlyene oxide), poly(ethylene oxide), and poly(oligo(ethylene glycol)methacrylate) (POEGMA); and the hydrophobic block is one or more selected from the group consisting of poly(styrene), poly(isoprene), and poly(methyl methacrylate).

13. The method of claim 8, wherein the solution mixture comprises, based on 100 parts by weight of a solvent, 0.5-30 parts by weight of the electroconductive precursor, 0.5-30 parts by weight of the pore support precursor, and 0.5-10 parts by weight of the continuous pore forming agent.

14. The method of claim 8, wherein a size of the continuous pores ranges from 1 to 1000 nm, and at least some of the continuous pores are connected with each other.

15. The method of claim 8, further comprising a step of removing the pore support precursor between steps (3) and (4).

16. The method of claim 8, wherein the catalyst is an enzyme or a metal catalyst.

* * * * *

UNITED STATES PATENT AND TRADEMARK OFFICE
CERTIFICATE OF CORRECTION

PATENT NO. : 10,141,577 B2
APPLICATION NO. : 14/113442
DATED : November 27, 2018
INVENTOR(S) : Jungbae Kim et al.

Page 1 of 1

It is certified that error appears in the above-identified patent and that said Letters Patent is hereby corrected as shown below:

On the Title Page

Under ABSTRACT "16 Claims, 11 Drawing Sheets" should read --15 Claims, 11 Drawing Sheets--.

In the Claims

Column 20, Lines 20-27 should read:

--14. The method of claim 8, further comprising a step of removing the pore support precursor between steps (3) and (4).

15. The method of claim 8, wherein the catalyst is an enzyme or a metal catalyst.--.

Signed and Sealed this
Twenty-sixth Day of November, 2019

Andrei Iancu
*Director of the United States Patent and Trademark Office*